(12) United States Patent
Loing

(10) Patent No.: US 10,004,678 B2
(45) Date of Patent: Jun. 26, 2018

(54) ANTI-DANDRUFF COMPOSITIONS, AND METHODS OF USE THEREOF

(71) Applicant: LUCAS MEYER COSMETICS CANADA INC., Québec (CA)

(72) Inventor: Estelle Loing, Québec (CA)

(73) Assignee: Lucas Meyer Cosmetics Canada Inc. (CA)

( * ) Notice: Subject to any disclaimer, the term of this patent is extended or adjusted under 35 U.S.C. 154(b) by 145 days.

(21) Appl. No.: 14/907,497

(22) PCT Filed: Aug. 21, 2014

(86) PCT No.: PCT/CA2014/050804
§ 371 (c)(1),
(2) Date: Jan. 25, 2016

(87) PCT Pub. No.: WO2015/024128
PCT Pub. Date: Feb. 26, 2015

(65) Prior Publication Data
US 2016/0184216 A1  Jun. 30, 2016

Related U.S. Application Data

(60) Provisional application No. 61/905,372, filed on Nov. 18, 2013, provisional application No. 61/868,744, filed on Aug. 22, 2013.

(51) Int. Cl.
| | | |
|---|---|---|
| *A61K 36/00* | (2006.01) | |
| *A61K 8/97* | (2017.01) | |
| *A61K 36/185* | (2006.01) | |
| *A61Q 5/00* | (2006.01) | |
| *A61Q 5/02* | (2006.01) | |

(52) U.S. Cl.
CPC .............. *A61K 8/97* (2013.01); *A61K 36/185* (2013.01); *A61Q 5/006* (2013.01); *A61Q 5/008* (2013.01); *A61Q 5/02* (2013.01); *A61K 2800/40* (2013.01)

(58) Field of Classification Search
CPC .................................................. A61K 36/00
See application file for complete search history.

(56) References Cited

U.S. PATENT DOCUMENTS 6,528,490 B2  3/2003  Steck et al.

FOREIGN PATENT DOCUMENTS

| CA | 2386648 A1 | 11/2003 | |
|---|---|---|---|
| EP | 0234019 A1 | 9/1987 | |
| FR | 2867973 A1 * | 9/2005 | ............... A61K 8/97 |
| JP | 2003277280 A * | 10/2003 | |
| WO | 0119377 A1 | 3/2001 | |

OTHER PUBLICATIONS

Broecks et al., "Cosmetic intolerance", Contact Dermatitis, 1987, 16: 89.
Helsinki, World Medical Association Declaration of Helsinki/Ethical Principles for Medical Research Involving Human Subjects—Helsinki Declaration (1964) and its successive updates.
ICH Topic E6/ Note for guidance on Good Clinical Practice, 1997, CPMP / ICH / 135 / 95.
Lentner et al., "A new method for assessing the gloss of human skin". Skin Pharmacology, 1996; 9,3: 184-189.
In Ro B. et al., "The role of sebaceous gland activity and scalp microfloral metabolism in the etiology of seborrheic dermatitis and dandruff" J Investig Dermatol Symp Proc. 2005, 10(3):194-7.
Robert et al., "Dermopharmacologie clinique", Edisem Maloine, 1985.
Smith et al., "Thematic review series: skin lipids. Sebaceous gland lipids: friend or foe?" J Lipid Res. 2008; 49 (2):271-81. Epub Nov. 1, 2007.
Sokal et al., "Biometry : the principles and practice of statistics in biological research—3nd edn", W.H. Freeman and company, New York, 1995.
International Search Report in PCT/CA2014/050804 to Lucas Meyer Cosmetics Canada Inc., dated Nov. 20, 2014.
Granica, S et al. "Phytochemistry, pharmacology and traditional uses of different *Epilobium* species (Onagraceae): A review", J Ethnopharmacol. vol. 156, pp. 3 J 6-346, Oct. 28, 2014.
Kosalec, I et al. "Antimicrobial activity ofwillowherb (*Epilobium angustifolium* L.) leaves and tlowers", Curr. Drug Targets. vol. 14, No. 9, pp. 986-991, Aug. 2013.
Pure & Basic, Natural Anti-Dandruff Shampoo, Tea Tree & Rosemary, 12 fl oz (350 ml). The product overview [online]. iHerb.com, [web pages cached by Internet Archive's Wayback Machine on Apr. 23, 2013]. [Retrieved on Nov. 10, 2014, total of 2 pages]. Retrieved from the Internet: <URL: https://web.archive.org/web/20130423173914/http://www.iherb.com/Pure-Basic-Natural-AntiDandruff-Shampoo-Tea-Tree-Rosemary-12-fl-oz-350-ml/8660>.
Hiermann, A. EP 0234019 A1; Sep. 2, 1987 (English Translation).
Daniel E.M. et al., 1991, The Effects of pH and Rat Intestinal Contents on the Liberation of Ellagic Acid From Purified and Crude Ellagitannins, J. Natural Products 54(4):946 (1st page).
Extended European Search Report for Application No. EP14837861 dated Oct. 17, 2016.

* cited by examiner

*Primary Examiner* — Qiuwen Mi
(74) *Attorney, Agent, or Firm* — Lerner, David, Littenberg, Krumholz & Mentlik, LLP

(57) ABSTRACT

An anti-dandruff composition comprising an *Epilobium angustifolium* extract, methods of use thereof and kits using same.

17 Claims, 9 Drawing Sheets

ANTI-DANDRUFF COMPOSITIONS, AND METHODS OF USE THEREOF

CROSS-REFERENCE TO RELATED APPLICATIONS

This application is a national phase entry under 35 U.S.C. § 371 of International Application No. PCT/CA2014/050804 filed on Aug. 21, 2014 and published in English, which claims benefit of the filing date of U.S. provisional application Ser. No. 61/868,744, filed on Aug. 22, 2013 and Ser. No. 61/905,372, filed on Nov. 18, 2013 the disclosures of which are hereby incorporated herein by reference.

STATEMENT REGARDING FEDERALLY SPONSORED RESEARCH OR DEVELOPMENT

N.A.

FIELD OF THE INVENTION

The present invention relates to anti-dandruff compositions and methods of use thereof. More specifically, the present invention is concerned with anti-dandruff compositions comprising an *Epilobium angustifolium* extract, methods of uses thereof and kits thereof.

BACKGROUND OF THE INVENTION

Dandruff or *pityriasis capitis* is the most widespread and under-diagnosed scalp problem worldwide. It will affect about half of Caucasians to some degree before they reach 20 years old.

It is characterized by discarded stratum corneum clumped into oily white flakes. In normal scalp, skin migration is about 28 days and cells shed as single cells, while in scalps with dandruff, cell migration is of about 7 to 21 days and cells shed in clumps of about 100-1000 cells. Although the precise link between the *Malassezia* fungus and dandruff is unclear, it is recognized that this fungus contributes to dandruff as follows: *Malassezia* which requires fat to grow, uses different types of lipase to hydrolyze triglycerides on the scalp surface (e.g., on comeocytes), the hydrolysis releases unsaturated fatty acid which in turn increases *Malassezia* growth and may cause inflammation and itching. *Malassezia* represents about 46% of the microflora in normal subjects, and about 74% of the microflora in subjects with dandruff. The species *Malassezia globosa* and *restricta* are reported to be the dominant species present in the human scalp, with *M. globosa* being the species with the highest lipase activity. *Malassezia*'s presence alone is reported not be sufficient to cause dandruff, however.

Other contributing factors include genetic predisposition, androgenetic metabolism (i.e., hormonal change), psychological stress, environmental irritants (pollution, high humidity, temperature, UV radiation) and cosmetics.

Current anti-dandruff ingredients attempt to control lipase activity, sebum, fungus or inflammation, and/or include keratolytic, anti-microbial/anti-fungal, or anti-proliferative agents. Keratolitic agents (e.g., salicylic acid (Sebex™, Sebulex™, Neutrogena™ T/Sal)) will remove a considerable proportion of flakes in patients with milder conditions. The majority of commercially available dandruff treatments include anti-microbial/anti-fungal agents, which have been shown to improve the visible symptom of flaking and restore the underlying skin condition (Warner et al., 2001). For example, these agents include pyrithione zinc (Selsun Blue™ for Itchy Dry Scalp, Neutrogena™ T/Gel Daily Control Dandruff Shampoo, Head & Shoulders™), selenium sulfide (Dandrex™, Head & Shoulders™ Clinical Strength, Selsun™), ketoconazole (Extina™, Nizoral™ A-D, Xolegel™), and ciclopirox. Anti-proliferative agents (e.g., coal tar (Denorex Therapeutic Protection™, Neutrogena™ T/Gel, Scytera™)) decrease epidermal proliferation and dermal infiltrates (Schwartz et al., 2004). Adjunctive treatment with topical steroids may also be helpful in patients whose condition includes evidence of an inflammatory component. Given that many subjects with dandruff may require regular, long-term use of therapeutic agents, it is important that the treatments be formulated so as to be aesthetically and cosmetically acceptable to the patient.

There are a number of potential disadvantages associated with current dandruff treatments. For example, while coal tar works as both an anti-dandruff agent and a biocide, it is a known carcinogen that may be toxic to the skin's health. In fact, the Environmental Working Group's cosmetic safety database ranks it a 10 on a scale of 0 to 10, with 10 being the most hazardous to health. Accordingly, coal tar is banned in various geographic regions such as Canada and the European Union, although it is available in over-the-counter shampoos in the United States. Some people may be allergic to zinc pyrithione, or may experience skin irritation caused by this ingredient, although both of these side effects are very rare, according to Drug Information Online. Zinc pyrithione may also irritate eyes on contact and can cause nausea if swallowed, according to the National Library of Medicine's Households Products Database. Salicylic acid may help with dandruff by loosening dead skin crusts. However, a stinging or burning sensation may be experienced when applying a shampoo containing the acid, and it may irritate skin, according to the National Institutes of Health. More serious, potential side effects may include vomiting, dizziness and changes in breathing rates, though such effects are rare. Some people may be allergic to selenium according to the National Institutes of Health (NIH). The NIH also reports that skin irritation, rashes and other topical side effects are most often associated with shampoos containing selenium at a strength of 2.5 percent or higher. Ketoconazole may prompt itching of skin, hives and a rash when using topically, according to the NIH. More serious side effects, such as an increased risk of cancer, are related to internal ingestion of the chemical.

Although the above mentioned chemicals have been reported to show some efficacy, it may be advantageous to reduce their concentration in an anti-dandruff treatment (e.g., by combining them with other active ingredients) to decrease the risk of triggering their potential side effects. Furthermore, due to health and environmental concerns, as well as increasing pressure from consumers, naturally-derived and/or eco-friendly anti-dandruff active ingredients would be highly desirable.

The present description refers to a number of documents, the content of which is herein incorporated by reference in their entirety.

SUMMARY OF THE INVENTION

More specifically, in accordance with the present invention, there is provided an anti-dandruff composition comprising an *Epilobium angustifolium* extract. In another specific embodiment, the *Epilobium angustifolium* extract is an aqueous extract. In another specific embodiment, the *Epilobium angustifolium* extract is present at a concentration sufficient to inhibit growth of a *Malassezia* fungus. In another specific embodiment, the *Malassezia* fungus is: *Malassezia furfur, Malassezia globosa, Malassezia restricta*, or any combination thereof. In specific embodiments, the above mentioned composition comprises at least 0.23%, at least 0.25%, or at least 0.46% (w/v) of dry weight *Epilobium angustifolium* extract.

In a specific embodiment, the composition further comprises a physiologically acceptable carrier. In another specific embodiment, the composition comprises an emulsified oil. In another specific embodiment, the composition comprises a preservative (e.g., sodium metabisulfite and/or phenoxyethanol). In another specific embodiment, the composition is formulated as a shampoo, a spray, a cream, a lotion, a mask, or a gel. In another specific embodiment, the composition further comprises at least one other agent useful to treat or prevent a scalp condition or disorder or at least one symptom thereof. In another specific embodiment, the at least one other agent useful to treat or prevent a scalp condition or disorder or at least one symptom thereof is an anti-dandruff agent, an anti-sebum agent, an anti-irritation agent, an antioxidant agent, an anti-erythema agent, an anti-fungal agent, an anti-inflammation agent, or an anti-lipase agent.

In a specific embodiment, the above mentioned composition is for use in reducing or preventing dandruff, such as adherent dandruff; non-adherent dandruff; or a combination thereof. In another specific embodiment, the above mentioned composition is for further use in reducing or preventing at least one of: hair regreasing; scalp irritation; scalp erythema; and scalp itching.

In accordance with another aspect of the present invention, there is provided a method for reducing or preventing dandruff, the method comprising applying the composition as defined above on the scalp of a subject in need thereof, wherein the dandruff is reduced on the scalp of the subject as compared to prior to the administration. In some embodiments, the dandruff is: adherent dandruff; non-adherent dandruff; or a combination thereof. In some embodiments, the above mentioned composition is further for reducing or preventing at least one of: hair regreasing; scalp irritation; scalp erythema; and scalp itching.

In accordance with another aspect of the present invention, there is provided a method of using (i) the composition of the present invention; or (ii) an *Epilobium angustifolium* extract; for reducing or preventing (a) adherent dandruff; (b) non-adherent dandruff; or (c) a combination of (a) and (b), comprising administering the composition or extract on the scalp of a subject in need thereof, whereby (a), (b) or (c) is reduced in the subject as compared to in the subject prior to said administration. In a specific embodiment, the composition or extract is further for reducing or preventing at least one of (e) hair regreasing; (f) scalp irritation; (g) scalp erythema; and (h) scalp itching. In another specific embodiment, said composition or extract is applied at least three times on the scalp of the subject.

In another specific embodiment, said composition or extract is applied every 3 days over at least 9 days. In another specific embodiment, said composition or extract is applied every 3 days over at least 12 days. In another specific embodiment, said composition or extract is applied every 3 days over at least 15 days. In another specific embodiment, said composition or extract is applied every 3 days over at least 18 days. In another specific embodiment, said composition or extract is applied every 3 days over at least 21 days. In another specific embodiment, said composition or extract is applied every 3 days over at least 24 days. In another specific embodiment, said composition or extract is applied every 3 days over at least 27 days. In another specific embodiment, said composition or extract is applied every 3 days over at least 30 days.

In accordance with another aspect of the present invention, there is provided a use of (i) the composition of the present invention; or (ii) an *Epilobium angustifolium* extract; for reducing or preventing or for the manufacture of a medicament for reducing or preventing (a) adherent dandruff; (b) non-adherent dandruff; or (c) a combination of (a) and (b). In a specific embodiment, the composition or extract is further for reducing or preventing at least one of (e) hair regreasing; (f) scalp irritation; (g) scalp erythema; and (h) scalp itching.

In some aspects, the present invention relates to the use of the composition as defined above, for reducing or preventing dandruff. In some aspects, the present invention relates to the use of the composition as defined above, for the manufacture of a medicament for reducing or preventing dandruff. In some embodiments, the dandruff is: adherent dandruff; non-adherent dandruff; or a combination thereof. In some embodiments, the above mentioned use is also for reducing or preventing at least one of: hair regreasing; scalp irritation; scalp erythema; and scalp itching.

In accordance with another aspect of the present invention, there is provided a composition comprising (i) the composition of the present invention; or (ii) an *Epilobium angustifolium* extract; for reducing or preventing or for the manufacture of a medicament for reducing or preventing (a) adherent dandruff; (b) non-adherent dandruff; or (c) a combination of (a) and (b). In a specific embodiment, the composition or extract is further for reducing or preventing at least one of (e) hair regreasing; (f) scalp irritation; (g) scalp erythema; and (h) scalp itching.

In accordance with another aspect of the present invention, there is provided a kit comprising (A) the composition of the present invention or an *Epilobium angustifolium* extract; and (B) at least one of: (i) instructions to use (A) for reducing or preventing dandruff (e.g., adherent dandruff, non-adherent dandruff, or a combination thereof); and (ii) at least one other agent useful to treat or prevent a scalp condition or disorder or at least one symptom thereof. In a specific embodiment, the at least one other agent useful to treat or prevent a scalp condition or disorder or at least one symptom thereof is an anti-dandruff agent, an anti-irritation agent; an antioxidant agent, an anti-sebum agent, an anti-fungal agent, an anti-inflammation agent, an anti-lipase agent.

Other features of the present invention will become more apparent upon reading of the following non-restrictive description of specific embodiments thereof, given by way of example only with reference to the accompanying drawings.

DESCRIPTION OF ILLUSTRATIVE EMBODIMENTS

Anti-Dandruff Compositions

Figure 1:
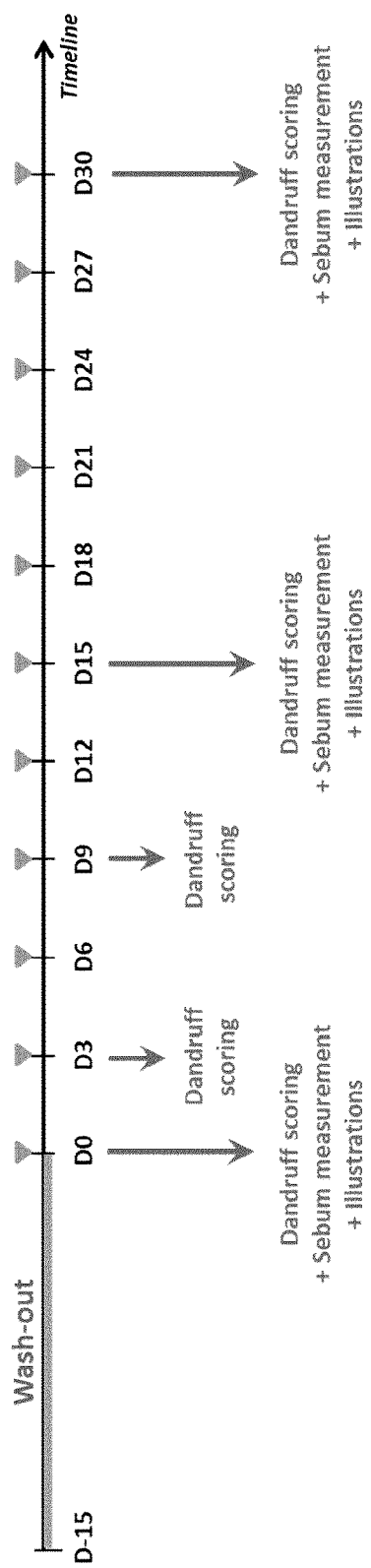
FIG. 1 schematically presents a timeline of the clinical protocol followed to test the anti-dandruff activity of the *E. angustifolium* extract-containing active shampoo prepared as described in Example 2. The neutral shampoo was used every 3 days during the wash out period, while the active shampoo (comprising the *E. angustifolium* extract) was used from D3 every three days.

Anti-dandruff compositions of the present invention comprise an *Epilobium angustifolium* extract (also sometimes called *Chamerion angustifolium*, rosebay willowherb, fireweed (mainly in North America), or Great Willow-herb (some parts of Canada)).

They may take the form of a wet or dry shampoo, of a leave on formulation (e.g., spray, cream, etc.), a mask, a lotion, etc.

Components of Anti-Dandruff Compositions

Certain embodiments of the anti-dandruff compositions of the present invention may further include one or more optional components known for use in hair care provided that the optional components are chemically and physically compatible with the compositions described herein, or do not otherwise unduly impair product stability, aesthetics or performance. Individual concentrations of such optional components may typically range from about 0.001% to about 10% w/w of the composition.

In some embodiments, compositions of the present invention comprise a concentration of *Epilobium angustifolium* extract sufficient to scavenge free radicals. In some embodiments, compositions of the present invention comprise a concentration of *Epilobium angustifolium* extract sufficient to inhibit growth of a *Malassezia* fungus (e.g., *Malassezia furfur, Malassezia globosa, Malassezia restricta*, or any combination thereof). In some embodiments, compositions of the present invention comprise at least 0.23%, 0.25%, or 0.46% (w/v) of dry weight *Epilobium angustifolium* extract (dry extract). In some embodiments, compositions of the present invention comprise at least 0.2%, 0.25%, 0.3%, 0.35%, 0.4%, 0.45%, 0.5%, 0.55%, or 0.6% (w/v) of dry weight *Epilobium angustifolium* extract (dry extract).

In some embodiments, compositions of the present invention may comprise a physiologically (or pharmaceutically) acceptable carrier.

In some embodiments, compositions of the present invention may comprise an emulsified oil.

Non-limiting examples of optional components for use in the composition include dispersed particles, cationic polymers, other conditioning agents (hydrocarbon oils, fatty esters, other silicones), suspending agents, viscosity modifiers, dyes, nonvolatile solvents or diluents (water soluble and insoluble), pearlescent aids, foam boosters, additional surfactants or nonionic cosurfactants, pediculocides, pH adjusting agents, perfumes, preservatives (sodium metabisulfite, phenoxyethanol), chelants, proteins, skin active agents, sunscreens, UV absorbers, and vitamins.

In specific embodiment, they may comprise at least one other agent useful to reduce or prevent a scalp condition or disorder or at least one symptom thereof. In more specific embodiment, at least one other agent useful to treat or prevent a scalp condition or disorder or at least one symptom thereof may be at least one of an anti-dandruff agent, an anti-sebum agent, an anti-irritation agent; an antioxidant agent, anti-erythema agent, an anti-fungal agent, an anti-inflammation agent, and an anti-lipase agent, etc.

Anti-dandruff agents: Suitable, non-limiting examples of additional anti-dandruff agents include: antifungal agents such as selenium sulfide, azoles (e.g., ketoconazole), particulate sulfur, ciclopirox, pyridinethione salts; keratolytic agents such as salicylic acid; and mixtures of at least two of the foregoing ingredients.

Anti-irritation agents: Suitable, non-limiting examples of anti-irritation agents include: oenothein A and/or B as described in U.S. Pat. No. 6,528,490 to Steck et al.

Additional anti-inflammation agents: Suitable, non-limiting examples of anti-irritation agents include: oenothein A and/or B as described in U.S. Pat. No. 6,528,490 to Steck et al.

Additional anti-oxidant agents: Suitable, non-limiting examples of anti-irritation agents include: oenothein A and/or B as described in U.S. Pat. No. 6,528,490 to Steck et al.

Extracts

In accordance with an embodiment of the present invention, there are provided anti-dandruff compositions comprising an extract from an *Epilobium angustifolium* and methods of using an *Epilobium angustifolium*.

Preparation of Extracts

In accordance with certain embodiments of the present invention, plants and/or plant parts (e.g., flowers, leaves and/or stems) can be isolated and ground (e.g., coarsely grinded using an electrical blender or mortar and pestle) and/or dried before being powdered/crushed. Other methods known in the art for grinding may be used. The plant material may then be subjected to a solvent extraction process.

In accordance with an embodiment of the invention, *Epilobium angustifolium* material (e.g., fresh or dry, crushed or not) may be subjected to e.g., a decoction, reflux, an infusion or the use of supercritical $CO_2$.

As used herein the term "decoction" is meant to refer to a process of extracting by boiling, dissolved chemicals from plant material (e.g., flowers, leaves, stems, roots, bark, rhizomes, etc.). Decoction involves boiling in a solvent (e.g., aqueous solvent, alcoholic solvent, hydroalcoholic solvent, organic solvent, a mix of at least two thereof, etc.) to extract oils, volatile organic compounds, and other chemical substances from the *Epilobium angustifolium*.

In an embodiment of the invention, the following decoction procedure may be used: the *Epilobium angustifolium* material (e.g., dried plant powder) may be heated (e.g., boiled, or heated at a temperature between about 60 and about 100° C., or between about 70 and about 100° C., or between about 80 and about 100° C., or between about 85 and about 100° C., or between about 85 and about 95° C.) in a solvent (e.g., aqueous solvent, alcoholic solvent, hydroalcoholic solvent, organic solvent, a mix of at least two thereof, etc.) for a time sufficient to extract useful plant components (e.g., about 30 minutes to about 5 hours) and the obtained solution can be decanted and/or filtered. The decoction procedure can be repeated a number of times (e.g., 1, 2, 3, 4, 5 or more) and the result of the successive extractions can be collected and combined.

In accordance with another embodiment of the invention, *Epilobium angustifolium* material (e.g., fresh or dried, ground or not) may be subjected to a reflux. As used herein the term "reflux" is meant to refer to a process of extracting chemicals from plant material (e.g., flowers, leaves, stems, roots, bark, rhizomes, etc.) by heating the plant material in a solvent (e.g., aqueous solvent, alcoholic solvent, hydroalcoholic solvent, organic solvent, a mix of at least two thereof, etc.) to create vapors, condensing the vapors and returning this condensate to the mixture of plant and solvent from which it originated. The reflux is a variant of the decoction.

In an embodiment of the invention, the following reflux procedure may be used: *Epilobium angustifolium* material (e.g., fresh or dried, ground or not) may be used. If ground material is used, it may first optionally be sifted with a filter (e.g., 1 to 4 mm mesh). The material (filtrated or not) can be used for the extraction. The plant material can be mixed with a solvent in a container and refluxed for a time sufficient to extract chemicals (e.g., about 30 minutes to about 3 hours)—i.e., the mixture can be boiled and the vapor captured in a condenser set up to return the condensed distillate to the container. The mixture can then be filtered, the filtrate recovered and the plant residue left in the container. The reflux procedure may be repeated a number of times (e.g., 1, 2, 3, 4, 5 or more) and the resulting extracts of the successive extractions can be collected and combined. The extracts can be evaporated to remove most alcohol if any (e.g., with a rotary evaporator). The aqueous phase can optionally be diluted with water and then frozen and lyophilized to obtain a powder.

In accordance with another embodiment of the invention, *Epilobium angustifolium* material (e.g., fresh or dried, ground or not) may be subjected to an infusion. As used herein the term "infusion" is meant to refer a process of extracting dissolved chemicals from plant material (e.g., flowers, leaves, stems, roots, bark, rhizomes, etc.) in a (heated or not) solvent (e.g., aqueous solvent, alcoholic solvent, hydroalcoholic solvent, organic solvent, a mix of at least two thereof, etc.), by allowing the material to remain suspended in the solvent over time (a process often called steeping) (e.g., at least 30 min, or at least 1 hour, or at least 2 hours, or at least 3 hours, or at least 4 hours, or at least 5 hours, etc.).

In an embodiment of the invention, the following infusion procedure may be used: a boiling solvent may be added to the *Epilobium angustifolium* material (e.g., fresh or dried, ground or not) and mixed for a time sufficient to extract chemicals (e.g., about 30 minutes to about 5 hours) at a temperature that allows the mixture to cool down (e.g., between about 10° C. and 40° C., preferably between 18° C. and 25° C.). The resulting infusion may be decanted and/or filtered. The infusion procedure can be repeated a number of times (e.g., 1, 2, 3, 4, 5 or more) and the result of the successive extractions can be collected and combined. Crude alcohol extracts may be concentrated under vacuum and subsequently lyophilised. Crude water extracts can be lyophilized.

The solvents that can be used for the extractions procedures (e.g., decoction or infusion or reflux or before and/or after the decoction or infusion or reflux) in accordance with the present invention include water (e.g., distilled and demineralised), hydroalcohol (i.e. mixture water and alcohol (e.g., water/alcohol of more than or about 10%, 20%, 30%, 40%, 50%, 60%, 70%, 80%, 90%), organic solvent, alcohol (e.g., ethanol), or any mixture of at least two of these solvents.

In a specific embodiment, a decoction or infusion or reflux may be followed by filtration and/or decantation of the solution to separate liquids from solids. Another treatment of the liquid and/or solid portion can also be performed. For example, the liquid portion can be treated to coagulate and/or precipitate mucilage and natural gums. Such treatments include the use of alcohol (e.g., ethanol) and activated carbon and decantation and/or filtration and/or diatomic earth to remove coagulated and/or precipitated mucilage and natural gums.

Hydroalcoholic and alcoholic extracts of the present invention may be an ethanolic or methanolic extract, propanolic, butanolic, glycerol, or an extract obtained from a $C_{1-10}$ aliphatic alcohol. In another embodiment, the extracts are obtained using an organic solvent, examples of which include ketones (such as $C_{1-10}$ ketones), hydrocarbons (such as hexane), organic acids, esters (such as ethyl acetate), ethers (such as ethyl ether), alkyl chlorides (such as methylene chloride), etc. A mixture of any two or more (e.g., 3 solvents, 4 solvents, etc.) of the foregoing solvents may be used with or without water (e.g., methanol and ethanol). The first solvent is evaporated to generate a first extract/residue.

As use herein, the phrase "aqueous extract" refers to a water-based preparation of *Epilobium angustifolium* material containing the biologically active portion (i.e., the compounds that reduce or prevent dandruff) without its cellular residue.

In some embodiments, *Epilobium angustifolium* solutions of the present invention comprise at least 1%, 1.5%, 2%, 2.5%, 3%, 3.5%, 4%, 4.5%, 5%, 5.5%, or 6% (w/w) of dry weight *Epilobium angustifolium* extract (dry extract).

Non-polar components/impurities. Additional extractions/suspensions may then be carried out to remove non-polar components/impurities of the first extract/residue. This additional extraction is performed with a second solvent (or mixture of solvents) on the first extract/residue obtained with the first solvent (or mixture of solvents). In an embodiment, the first extract/residue obtained with the first solvent (or mixture of solvents) is suspended in ethanol and extracted with an alkane that is non-soluble in methanol (e.g., hexane, pentane, or petroleum ether). The non-polar components/impurities are thus solubilized with the alkane (e.g., hexane) phase which is then discarded. The ethanol phase is then evaporated to generate a second extract/residue.

Polar components/impurities. In an embodiment, the second residue/extract obtained with the second solvent (or mixture of solvents) is subjected to a third suspension/extraction to remove polar components/impurities of the second extract/residue. For instance, the second extract/residue can be suspended in diethyl ether, butanol or chlorinated solvents such as chloroform or chloromethane and extracted with water. In an embodiment, the residue is suspended in $Et_2O$ and extracted with water. The polar components/impurities are thus solubilized with the water phase which is then discarded. The e.g., diethyl ether phase is then evaporated to generate a third extract/residue.

In more specific embodiments, the extract is an ethanolic extract, a methanolic extract, an hydroalcoholic (e.g., hydroethanolic extract) or a water extract of the plants of the present invention in liquid form or dried form. In embodiments, there is provided one or more fractions obtained by chromatographic separation of each extract of the present invention.

In embodiments, a preliminary extraction (i.e. prior to the first extraction (e.g., water, hydroalcoholic or alcoholic extraction)) can be performed on the plant material to remove undesirable compounds. For example, hexane or another solvent (e.g., hexane, ether, pentane or petroleum ether) could be used to remove non-polar compounds, such as waxy compounds. The first extraction can then be performed on the cleaned plant material.

In accordance with other embodiments of the present invention, alternatively to the solvent extract process, the extracts of the present invention can also be obtained through the use of supercritical $CO_2$. Supercritical extracts are often referred to as Super Critical Carbon Dioxide Extracts or $SCO_2$, because the process uses compressed carbon dioxide. Carbon dioxide is present in the air and is necessary for plant life. When it is compressed, it can turn into a liquid state. When pressure is increased, temperature increases. The super critical point is the exact temperature and pressure where a gas becomes a liquid. For carbon dioxide, it is relatively low (31 degrees Centigrade). The compressed $CO_2$ at this point has the density of a liquid, but the properties of a gas. The gas-like state helps the faster diffusion of the phytochemicals or extracts—almost two orders of magnitude higher than that of other liquids—while the liquid-like state helps in better solubility of the phytochemicals or extracts. Once the extraction is complete, the pressure is released, and the carbon dioxide is harmlessly freed. The extraction process starts with placing the raw botanical into an extractor. Liquid $CO_2$ is heated to its supercritical state (31 degrees Centigrade), and then pumped into the extractor. The $SCO_2$ then mixes with the botanical. The $SCO_2$, now carrying the desired extract, is transferred to a separator tank where pressure and temperature is controlled. The extract is precipitated in the separator, and $CO_2$ is recycled into the extractor via a condenser.

The extract can be in a liquid or dried form.

*Epilobium angustifolium* extracts of the present invention as used in methods of the present invention do not cause cutaneous intolerance.

*Epilobium angustifolium* extracts of the present invention encompass those commercialized by Lucas Meyer Cosmetics, A & E Connock, Bio-Botanica, Cosmetic Developments, Crodarom, IES Labo and Unipex for example.

Methods of Using Anti-Dandruff Compositions and Extracts of the Present Invention Extracts, molecules and compositions of the present invention are useful to reduce (a) adherent dandruff; (b) non-adherent dandruff; (c) scalp sebum; (d) scalp regreasing; (e) scalp irritation; (f) scalp itching; (g) scalp erythema; (h) scalp redness; (i) scalp inflammation; or (j) at least two of (a) to (i). In a specific embodiment, it reduces at least (a) or (b). In another specific embodiment, it reduces at least (a) or (b) and further reduces at least one of (c) to (i). In a specific embodiment, the subject has sensitive skin.

As used herein, the term "reduce" or "reducing" is meant to refer to a reduction of a pre-existing scalp condition or disorder. It encompasses complete or partial correction/treatment (e.g., reduction of severity or frequency) of the scalp skin condition or disorder. As used herein, the term "preventing" in the expression "preventing scalp condition or disorder" (e.g., dandruff, scalp regreasing, etc.) is meant to refer to a delay in the initiation of, or a complete or partial prevention (e.g., reduction of severity or frequency) of a scalp condition or disorder or of at least one symptom thereof (e.g., adherent dandruff, non-adherent dandruff, scalp sebum, scalp erythema, scalp irritation, etc.). As used herein, a "reduction" corresponds to a decrease of at least 5%, 10%, 15%, 20%, 25%, 30%, 40%, 45%, 50%, 55%, 60%, 65%, 70%, 75%, 80%, 85%, 90%, 95%, 100%, 150%, 200%, 250%, or 300%, etc. of at least one symptom in the treated subject as compared to the symptom in the subject prior to the treatment. In the case of reduction of dandruff (adherent or non-adherent) or irritation or erythema, a reduction may also mean a reduction in the score (e.g., reduction of 0.5, 1, 1.5, 2, 2.5, 3, 3.5, 4, 4.5 or 5 score unit(s) as described herein).

As used herein, a "prevention" may correspond to a delay in the occurrence or reoccurrence of scalp condition or disorder or of at least one symptom thereof in the subject after treatment with the composition or extracts of the present invention (e.g., hair washing with shampoo comprising *Epilobium angustifolium* extract of the present invention) of at least 5%, 10%, 15%, 20%, 25%, 30%, 40%, 45%, 50%, 55%, 60%, 65%, 70%, 75%, 80%, 85%, 90%, 95%, 100%, 150%, 200%, 250%, or 300%, etc. (or 1, 2, 3, 4, 5 days, etc.) longer than the delay of occurrence or reoccurrence of the scalp condition or disorder or of at least one symptom thereof in an subject after hair washing without the active ingredient of the present invention (e.g., neutral shampoo (i.e., without *Epilobium angustifolium* extract)).

A "therapeutically effective amount" refers to an amount effective, at dosages and for periods of time necessary, to achieve the desired therapeutic result, such as reduction of a scalp condition or disorder or of a symptom thereof (e.g., dandruff). A therapeutically effective amount of *Epilobium angustifolium* may vary according to factors such as the disease state, age, sex, and weight of the individual, and the ability of the *Epilobium angustifolium* extract to elicit a desired response in the individual. Dosage regimens may be adjusted to provide the optimum therapeutic response. A therapeutically effective amount is also one in which any toxic or detrimental effects of the *Epilobium angustifolium* extract are outweighed by the therapeutically beneficial effects.

A "prophylactically effective amount" refers to an amount effective, at dosages and for periods of time necessary, to achieve the desired prophylactic result, such as preventing a scalp condition or disorder or of a symptom thereof (e.g., dandruff, regreasing, etc.). A prophylactically effective amount can be determined as described above for the therapeutically effective amount.

In particular embodiments, a preferred range for therapeutically or prophylactically effective amount of *E. angustifolium* extract may be about 0.1% to about 10% by weight of the composition, in a specific embodiment, it may be between about 1% and about 7% by weight of the composition, or between about 1% and about 5% by weight of the composition, or between about 1% and about 4% by weight of the composition, or between about 1% and about 3% by weight of the composition, or between about 1% and about 2% by weight of the composition. One method of cosmetic, prophylactic or therapeutic treatment is to apply an *Epilobium angustifolium* extract topically to the scalp in e.g., as a shampoo or as a leave on composition. Dosage values may vary with the severity of the condition to be alleviated. It is to be further understood that for any particular subject, specific dosage regimens may be adjusted over time according to the individual need and the judgment of the person administering or supervising the administration of the compositions, and that dosage ranges set forth herein are exemplary only and are not intended to limit the scope or practice of the methods of the invention.

In accordance with another aspect of the invention, therapeutic compositions of the present invention, comprising an *Epilobium angustifolium* extract, may be provided in containers having labels that provide instructions for use of the formulation to e.g., reduce dandruff, scalp seborrhea, scalp irritation, scalp erythema, scalp redness, or scalp itching. The labels may also disclose that the compositions comprise at least one other active ingredient useful to reduce at least one of the foregoing symptom or condition (e.g., anti-dandruff agent (e.g., salicylic acid, anti-irritant, anti-inflammatory or anti-oxidant (e.g., oenothein), etc.).

As used herein "pharmaceutically acceptable carrier" or "physiologically acceptable carrier" or "excipient" includes any and all creams, gels, solvents, dispersion media, coatings, antibacterial and antifungal agents, isotonic and absorption delaying agents, and the like that are physiologically compatible and do not significantly adversely affect the pharmaceutical properties (e.g. toxicity and effectiveness) of the *Epilobium angustifolium*, such as are conventionally used in the cosmetic and pharmaceutical arts. In one embodiment, the carrier is suitable for topical administration. In some embodiments, topical administration includes administration to the scalp. Under some conditions, active molecules in the *Epilobium angustifolium* extract may undergo hydrolysis in acid or base, so that pharmaceutically or physiologically acceptable carriers or excipients may include pH buffers to maintain an acceptable pH for pharmaceutical activity (see Daniel et al., 1991, J. Natural Products 54(4):946, for a discussion of the effects of pH on ellagitannins).

Extracts, and hair and scalp compositions of the present invention are typically applied every day, two days, three days, four days, 5 days on the scalp of the subject or less frequently, or as often as required. They are also typically applied for a period of at least 1 week (or 2, 3, 4, 5, 6 weeks, etc.). They may also be applied for at least 7, 8, 9, 10, 11, 12, 13, 14, 15, 16, 17, 18, 19, 20, 21, 22, 24, 25, 26, 27, 28, 29, 30 days, etc. They may also be applied at least twice, three, four, five, six, seven, eight, nine, ten, eleven, twelve, thirteen, fourteen, fifteen, sixteen, seventeen, eighteen, nineteen, twenty times, etc. Treatment may be applied when at least one scalp condition or disorder or symptom thereof (e.g., dandruff) becomes detectable.

The present invention is illustrated in further details by the following non-limiting examples.

Example 1

*Epilobium angustifolium* Extract

*Epilobium angustifolium* plants were harvested, and their flowers, leaves and stems were homogenized and extracted in deionized water (prepared by reverse osmosis) at a water:plant ratio of 8:1 (w/w) for about 3 hours at a temperature of about 85° C. to 95° C. The solution was then clarified by decantation: the solids were separated from the liquid in a settling tank, and the liquid was then treated with ethanol and activated carbon to coagulate and precipitate mucilage and natural gums. The liquid was then filtered using a filter press to remove solids coagulated/agglomerated on the carbon. In cases where filtration was difficult, diatomic earth was optionally added on the filter press to facilitate filtration. Otherwise, filter paper was used on the retaining plates and filter pore size was adapted to remove visible precipitate on a centrifuged sample. Preservatives were then added (i.e., sodium metabisulfite (0.10-0.15%) and phenoxyethanol (0.60-0.75%)) to the filtrate and the solution was filtered again on 0.5 μm and 0.2 μm membrane filters in a controlled room subjected to HEPA air filtration. The following solution was obtained.

| Ingredients | % (w/w) |
|---|---|
| Water | 93-95 |
| *Epilobium angustifolium* flower/leaves and stem dry extract | 4.6-5.4 |
| Sodium Metabisulfite | 0.09-0.11 |
| Phenoxyethanol | 0.4-0.6 |

Example 2

Composition Comprising *Epilobium angustifolium* Extract

The table below provides the list and concentration of ingredients used in the "active" (phases A, B and C) and "neutral" (phases A and B) shampoos used in the clinical trial described in the Examples below.

| Phase | Ingredient | INCI name | % (w/w) |
|---|---|---|---|
| A | Deionized Water | Water | 78.15 |
|   | Dermofeel ™ PA-3 | Sodium Phytate, Water, alcohol | 0.10 |
|   | Ecogel ™ | Lysolecithin, *Sclerotium* Gum, Xanthan Gum, Pullulan | 0.50 |
| B | Dermosoft ™ G10LW | Polyglyceryl-10 Laurate, Water | 2.00 |
|   | Dermosoft ™ GMCY | Glyceryl caprylate | 1.00 |
|   | Tegobetain F50 | Cocamidopropyl Betaine | 4.45 |
|   | Texapon ™ N70 | Sodium Lauryl Ether Sulfate | 9.50 |
|   | Sodium Chloride | Sodium Chloride | 2.80 |
| C | *Epilobium angustifolium* solution prepared according to Example 1 | Water, *Epilobium angustifolium* flower/leaf/stem solution | 1.50 |
|   |   |   | 100% |

The neutral shampoo containing phases A and B was prepared as follows: Phase A was prepared by mixing water with Dermofeel™ PA-3, and heating the mixture to about 70-75° C. The Ecogel™ was added to the mixture and incorporated under agitation for 20 minutes or until all solids were dissolved. Phase B was prepared by mixing all of the ingredients (Dermosoft™ G10LW, Dermosoft™ GMCY, Tegobetain F50, Texapon™ N70, Sodium Chloride) to obtain a homogenous phase. The homogenous phase of phase B was then added to phase A, and the combination was mixed for about 5 minutes and then homogenized at 3000 rpm with an Ultra-Turrax™ dispersing instrument. The mixture was then cooled down until it reached less than about 40° C.

The active shampoo containing phases A, B and C was prepared as described above for the neutral shampoo, except that phase C (i.e., *Epilobium angustifolium* solution prepared as described in Example 1) was added after the final cooling step and the combination was mixed for about 5 minutes. The pH was adjusted if needed to reach between about 5.0 and 5.4. In some embodiments, the pH of the active shampoo may be between 4.3 and 5.5. In some embodiments, the pH of the active shampoo is about 5.1.

The neutral and active shampoos were stored at room temperature.

Example 3

*Malassezia* Species Growth Inhibition

Determination of the effectiveness of the solution prepared as described in Example 1 on 3 different *Malassezia* species was determined by measuring the lowest concentration of a molecule for which there is no visible growth of the microorganism strain (MIC). The *Malassezia* species used were *M. furfur* (strain 1634.86, Pasteur Institute), *M. globose* (strain IP 2387.96, Pasteur Institute), and *M. restricta* (strain 7877, Centralbureau voor Schimmerlcultures). Results are presented as a w/v concentration—i.e., 0.04% is 0.4 g/L; 0.078% is 0.78 g/L, 0.156% is 1.56 g/L and 0.25% is 2.5 g (dry weight)/L.

|  | *M. furfur* | *M. globosa* | *M. restricta* |
|---|---|---|---|
| *E. angustifolium* extract | 0.25% | 0.25% | 0.25% |
| Selenium disulfide (positive control) | 0.04% | 0.04% | 0.04% |
| Piroctone olamine (positive control) | 0.078% | 0.156% | 0.156% |

Example 4

Effect of *E. angustifolium* Extract on DPPH Scavenging Activity

DPPH (2,2-diphenyl-1-picrylhydrazyl), Trolox™ (reference) and ascorbic acid (positive control—not shown) were dissolved in alcohol at $5 \times 10^{-4}$ M, 10 g/L and $10^{-3}$ M, respectively. The *E. angustifolium* extract solutions as prepared in Example 1 were diluted directly in the reaction medium composed of alcohol, Tris-HCl buffer (0.1 N, pH 5.5) and the DPPH solution. The final concentration of DPPH was $10^{-4}$ M. The mixtures were shaken and left to stand for 30 minutes at room temperature in the dark. The absorbance at 540 nm by DPPH was then measured by a spectrophotometer (Berthold Mitras LB 240) at T=30 min, 2 hours, and 24 hours. The DPPH radical-scavenging activity was evaluated from the difference in absorbance of the DPPH detected at 540 nm between a blank and the *E. angustifolium* extract solutions.

Figure 7:
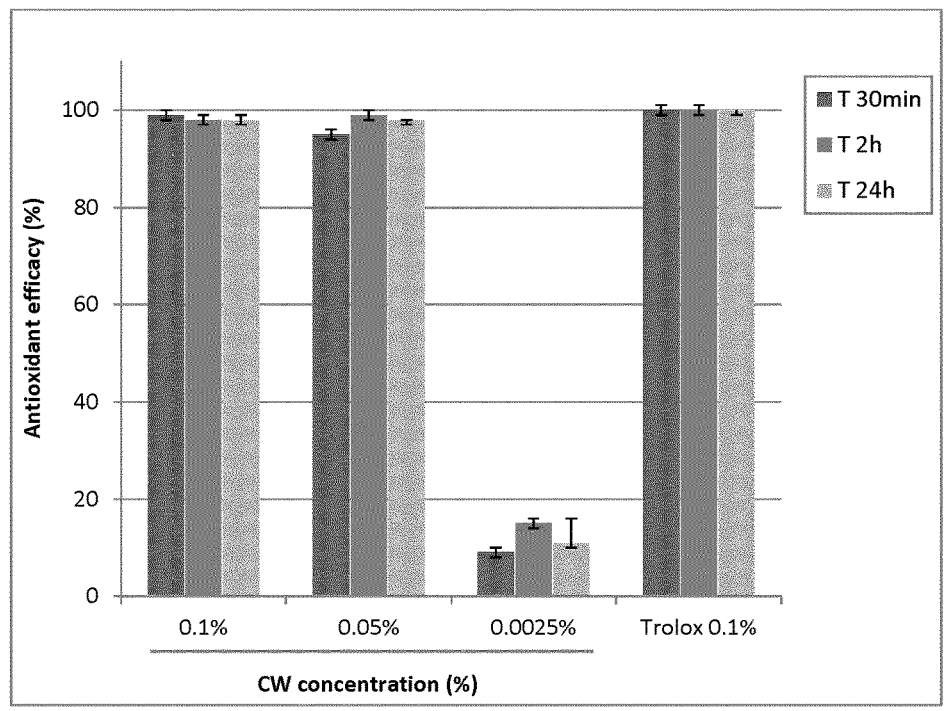
FIG. 7 presents the effect of the *E. angustifolium* solution prepared as described in Example 1 (also known as Canadian Willowherb™ (CW)) on DPPH scavenging activity.

FIG. 7 presents the results, which show that dilutions of the *E. angustifolium* solution prepared as described in Example 1 strongly reduces all types of free radicals at least at concentrations 0.1% (v/v) and 0.05% (v/v).

Example 5

Material and Methods for Clinical Trial

The studies described in Examples 6 to 13 herein were conducted according to the Helsinki Declaration (1964) and its successive updates. The system used for the study is certified ISO 9001:2008. It was an open, intra-individual study and each subject was its own control.

Subjects: Inclusion criteria: 24 male and female subjects having dandruff and greasy hair aged between 20 and 61 (average age 30±2 years) were used. They were healthy subjects, who gave their informed consent and were aware of the necessity and duration of controls so that a perfect adhesion to the protocol established by the clinical trial center could be expected. The subjects had washed their hair at least 72 hours before the measurement.

Non-inclusion criteria were subjects who that hair length smaller than 2 cm; alopecia in vertex, with frizzy hair influencing the scoring of dandruff; who had started, stopped or changed hormonal treatment (including contraceptive pills) in the previous six weeks; presenting antecedent of cutaneous allergy; who had used anti-dandruff, anti-hair loss or corticosteroid treatment for the scalp during the last two weeks before the start of the study; who has used products for the scalp (dyeing, bleaching, permanent waving and straightening, etc.) during the last week before D-15; practicing regularly a water sport and/or having regularly a sauna session; who is immunodepressed; who has undergone an operation in the month preceding the study; who used topical or systemic treatment liable to interfere with the assessment of the cutaneous tolerance of the product during the weeks preceding the study; who had excessive sun exposure during the month preceding study; who has a cutaneous pathology on the studied zone; who has taken drugs containing lithium, corticoids, anti-histaminic, anti-fungal, antibiotics, non-steroidal anti-inflammatory or immunosuppressive drugs during the month preceding study; who has taken retinoic acid in the 6-month period preceding the study; who enrolled in another clinical trial during the study; who is considered to be likely non-compliant to the protocol.

TABLE I

Subjects' demographic information

| Subject | Age | Sex | Scalp type | Hair type | Phototype* | Sensitive scalp |
|---|---|---|---|---|---|---|
| 1. | 61 | F | G | G | II | Yes |
| 2. | 23 | F | G | G | II | Yes |
| 3. | 24 | F | G | G | II | Yes |
| 4. | 24 | M | G | G | III | No |
| 5. | 24 | M | G | G | II | Yes |
| 6. | 24 | F | G | G | II | Yes |
| 7. | 44 | F | G | G | II | Yes |
| 8. | 44 | F | G | G | II | Yes |
| 9. | 28 | F | G | G | II | Yes |
| 10. | 20 | M | G | G | II | Yes |
| 11. | 22 | F | G | G | II | Yes |
| 12. | 42 | F | G | G | II | No |
| 13. | 25 | F | G | G | III | No |
| 14. | 22 | F | G | G | II | Yes |
| 15. | 28 | M | G | G | III | Yes |
| 16. | 24 | M | G | G | III | No |
| 17. | 36 | F | G | G | II | Yes |
| 18. | 20 | F | G | G | III | Yes |
| 19. | 26 | F | G | G | II | Yes |
| 20. | 23 | M | G | G | II | Yes |
| 21. | 22 | F | G | G | III | No |
| 22. | 22 | M | G | G | II | Yes |
| 23. | 24 | F | G | G | II | Yes |
| 24. | 60 | F | G | G | II | Yes |
| Mean | 30 | F 17 | N 0 | N 0 | I 0 | Yes 19 |
| Median | 24 | M 7 | D 0 | D 0 | II 18 | No 5 |
| Minimum | 20 |  | G 24 | G 24 | III 6 |  |
| Maximum | 61 |  |  |  | IV 0 |  |
| SEM | 2 |  |  |  |  |  |

Legend: M = male; F = female; N = normal; D = dry; G = greasy.
*I, II and III are skin types I, I and III, respectively.

The Fitzpatrick classification (Thomas B. Fitzpatrick, 1975) groups individuals according to the reaction of their skin to sun exposure. Phototype I: very fair skin, freckles, blond or red hair. Reaction to sun exposure: never tans, always burns. Phototype II: fair skin, blond or light brown hair, freckles appear when exposed to sun, light colored eyes. Reaction to sun exposure: tans with difficulty, and usually burns. Phototype III: fair skin, blond or light brown hair. Reaction to sun exposure: sometimes burns, progressively tans. Phototype IV: olive-skinned, light or dark brown hair; brown eyes. Reaction to sun exposure: rarely burns, tans easily. Phototype V: brown, dark brown skin, brown eyes. Reaction to sun exposure: very rarely burns, tans very easily. Phototype VI: very dark brown skin, brown eyes.

Reaction to sun exposure: never burns, tans very easily.

Subjects agreed not to use hair or scalp products other than those given for the study (including dyeing, bleaching, permanent waving and straightening, etc.), to keep a hair length>2 cm during the study, not to come with wet hair at study visits and not to regularly practice water sports and/or have regular sauna sessions.

On D-15 (±2 days): The subjects came to the laboratory without applying any product on the face since the previous evening (except the morning wash) and without wearing their contact lenses. They read, signed and dated the information sheet (instructions on the product use and restrictions related to the study) and informed consent forms in duplicate. These documents were also signed and dated by the person who conducted the informed consent discussion. The verification of inclusion and non-inclusion criteria under dermatological control: Clinical examination to assess the initial state of the scalp. The subjects were also asked about their usual unpleasant sensations. The neutral shampoo prepared as described in Example 2 was distributed to the subjects for use three times weekly for two weeks. The subjects received a daily log to write down their possible intolerance sensations or others.

On D0: Subjects returned to the laboratory without having applied any product on the hair and scalp since less than 72 hours before the visit. Clinical examination by the dermatologist to assess the initial state of the scalp. Dandruff, erythema and irritation scoring by the technician. Definition of one zone for sebum rate measurement using Sebumeter™ on a hair line. Measurement of the sebum rate using Sebumeter™ on the zone previously defined. Macrophotographs of the parting area (10 subjects only). Visia photographs (10 subjects). Hair washing with the active shampoo as described in Example 2 by the technician in charge of the study. Subjects received a new daily log to write down their possible intolerance sensations or others.

On D3: Subjects returned to the laboratory without having applied any product on the hair and scalp since the previous visit. They brought their daily log back to check the compliance. New clinical examination by the dermatologist to assess the state of the scalp. New dandruff, erythema and irritation scoring by the technician. New macrophotographs of the parting area (10 subjects). New Visia photographs (10 subjects). The active shampoo prepared as described in Example 2 was distributed to the subjects for use three times a week for 28 days.

On D9 (3 days after the third shampooing with the active shampoo product): Subjects returned to the laboratory without having applied any product on the hair and scalp since less than 72 hours before the visit. They brought their active shampoo product and daily log back in order to check the compliance. New clinical examination by the dermatologist to assess the state of the scalp. New dandruff, erythema and irritation scoring by the technician.

FIG. 1 schematically presents a timeline of the clinical protocol followed to test the anti-dandruff activity of the *E. angustifolium* extract in the context of an active shampoo prepared as described in Example 2. The timeline is described in more detail below.

On D15 (3 days after the fifth shampooing with the active shampoo product): Subjects returned to the laboratory without having applied any product on the hair and scalp since less than 72 hours before the visit. They brought their active shampoo product and daily log back in order to check the compliance. New clinical examination by the dermatologist to assess the state of the scalp. New dandruff, erythema and irritation scoring by the technician. New measurement of the sebum rate using Sebumeter® on the zone previously defined.

On D30 (3 days after the tenth shampooing with the active shampoo): Subjects returned to the laboratory without having applied any product on the hair and scalp since less than 72 hours before the visit. They brought their active shampoo product and daily log back in order to check the compliance. New clinical examination by the dermatologist to assess the final state of the scalp. New dandruff, erythema and irritation scoring by the technician. Measurement of the sebum rate using Sebumeter® on the zone previously defined. New Macrophotographs of the parting area (10 subjects). New Visia photographs (10 subjects). Subjects filled in the subjective evaluation questionnaire.

Trial period: the study started on Apr. 4, 2013 and finished on Jun. 5, 2013.

Clinical score of dandruff, erythema and irritation: The clinical evaluation was done on the head divided in four parts. The score of each criteria (Non-adherent and adherent dandruff, erythema, irritation) studied was the mean of the four parts scores (2 decimal places). Three days after the shampoo, a technician evaluated, under medical control, the non-adherent dandruff, adherent dandruff, the erythema and irritation using a score from 0 to 5.

TABLE II

Nature of scores for dandruff, erythema and irritation

| Score | Non-adherent dandruff | Adherent dandruff | Erythema | Irritations |
|---|---|---|---|---|
| 0 | no dandruff | no squamae | none | none |
| 1 | a few dispersed dandruff flakes | a few dispersed squamae flakes | very slight | very slight |
| 2 | a small quantity of dandruff | a small quantity of squamae | slight | slight |
| 3 | a moderate quantity of dandruff | a moderate quantity of squamae | moderate | moderate |
| 4 | a large quantity of dandruff | a large quantity of squamae | important | important |
| 5 | a very large quantity of dandruff | a very large quantity of squamae over the whole scalp | severe | severe |

The clinical "total dandruff score" was the sum of non-adherent and adherent dandruff.
The clinical "total erythema score" was the sum of erythema and irritation.

Sebo-regulating effect: The quantity of sebum excreted to the scalp skin surface was quantitatively evaluated with a COURAGE and KHAZAKA SM 810 PC Sebumeter™ on D0, D15 and D30 visits.

The Sebumeter™ is based on photometry. A synthetic ribbon, which becomes transparent when in contact with absorbed lipids, is applied to the measurement zone for precisely 30 seconds. Its transparency increases proportionally with the quantity of sebum from the hydrolipidic film with which it is in contact.

A reflectometry recording is used to quantify the increase of the light transmitted and to determine the total mass of the lipids excreted by the surface unit (in $\mu g/cm^2$).

Cutaneous tolerance: Before and after product uses, the subjects scalp was examined by the dermatologist to assess each of the following parameters: erythema, dryness, desquamation, seborrhea, dandruff, others with a score of none to severe (none, very slight, slight, moderate and severe), and the subject was also asked to score between none and severe, their sensation on D0: itching, stinging, warm or burning sensation, others.

On D30, the global cutaneous tolerance of the product was assessed by a clinical examination conducted by the dermatologist. This evaluation took into account the relevant signs reported by the subject (functional and physical signs=T1) as well as those noted during the examination (clinical signs=T2). The confrontation of these signs was used to conclude the final tolerance of the studied product. The global cutaneous tolerance of the studied product was defined as the least favorable result (T1 or T2). The relevance of a sign was defined as 1) lasting more than 5 minutes, 2) possible or certain imputability with the product (as opposed to null or doubtful imputability0; and 3) over a period superior or equal to a quarter of the length of the study.

Macrophotographs: On D0, D3 and D30 and in case of relapses, macrophotographs of one selected zone was taken. The digital camera used was camera of the type Nikon D90. The photographs were taken in standardized, indirect light. Aperture, speed and distance of the camera were standardized. The control of the repositioning will take place directly on data-processing screen thanks to a simultaneous visualization of the images at various times of acquisition.

The device used was the VISIA™ from CANFIELD™ imaging systems. The VISIA allows to take pictures with multiple lighting modes and a very rapid capture of images. The control of the repositioning takes place directly on data-processing screen using an overlay visualization of the images at each time of acquisition. A series of photos taken under multi-spectral imaging and analysis (white light, UV or polarized light-parallel or crossed) allowed to capture visual information. To visualize the dandruff, UV light was used.

Subjective evaluation: A subjective evaluation questionnaire prepared by the clinical trial center and submitted to the sponsor was filled in by the subjects on D30 to subjectively evaluate the properties of the studied product, efficacy, tolerance and its future use.

Statistical Method:

Statistical software: Microsoft® Excel 2010 and SAS™ 9.2.

A) For each following assessed criterion: adherent dandruff score, non-adherent dandruff score; and sebum measurement, the following descriptive statistics and comparative statistics were applied.

Descriptive statistics for quantitative variable were computed (number of values, number of missing values, mean, standard deviation, median, minimum value and maximum value) at each time point. The average evolution (±2 standard error of the mean) was plotted over time.

Comparative analysis: A mixed ANOVA model (proc GLM) for repeated measures (time as fixed factor and subject as random factor) was fitted to raw data. From this model, the comparison between each (Di) and the baseline value (D0) was performed using a Dunnett's test. The residual distribution was analyzed using Shapiro-Wilk test and graphical representations.

B) For each following assessed criterion: irritation score; and erythema score, the following descriptive statistics and comparative statistics were applied.

Descriptive statistics: The distribution of average score for each time point was computed (in frequency and percentage).

Comparative analysis: A linear model for categorical data (proc GENMOD) with factor time was carried out. From this model, the contrasts were built to compare each (Di) with the baseline value (D0).

For A) and B) analyses, the type I error probability was set at $a=0.05$ in a two tailed approach when applicable.

Example 6

Effect of *Epilobium angustifolium* Extract on Non-Adherent Dandruff

Three days after the last shampoo, the technician evaluated, under medical control, the non-adherent dandruff using a score from 0 to 5 according to Table II. The anti-non-adherent dandruff effect of the active shampoo prepared as described in Example 2 was evaluated at days D0, D3, D9, D15 and D30.

Figure 2:
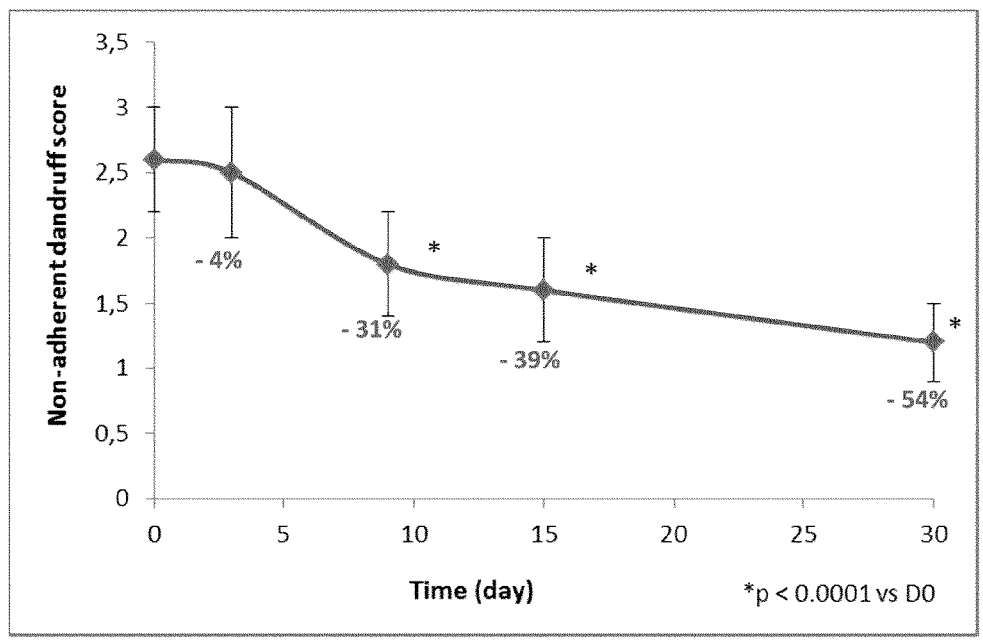
FIG. 2 presents the evolution of the average score (n=24) for non-adherent dandruff (±2 SEM) over time in human subjects treated with an active shampoo comprising the *E. angustifolium* extract prepared as described in Example 2.

The results are presented in Tables III and IV, as well as in FIG. 2.

TABLE III

Descriptive statistics for non-adherent dandruff score for each time point (Di).

| Time (Di) | N | N Missing | Mean | Median | Std Dev | Std Error | Minimum | Maximum |
|---|---|---|---|---|---|---|---|---|
| 0 | 24 | 0 | 2.6 | 2.5 | 0.8 | 0.2 | 1.5 | 4.5 |
| 3 | 24 | 0 | 2.5 | 2.5 | 1.0 | 0.2 | 1.0 | 4.5 |
| 9 | 24 | 0 | 1.8 | 2.0 | 0.9 | 0.2 | 0.3 | 4.0 |
| 15 | 24 | 0 | 1.6 | 1.5 | 0.9 | 0.2 | 0.0 | 3.0 |
| 30 | 24 | 0 | 1.2 | 1.0 | 0.6 | 0.1 | 0.0 | 2.0 |

TABLE IV

Summary of change from baseline for each time point (Di-D0), for non-adherent dandruff score

| Comparison (Di vs D0) | Estimate | SEM | Raw p | Adjusted p[1] |
|---|---|---|---|---|
| 3 vs 0 | −0.13 | 0.11 | 0.2769 | 0.6457 |
| 9 vs 0 | −0.79 | 0.11 | <.0001 | <.0001 |
| 15 vs 0 | −1.04 | 0.11 | <.0001 | <.0001 |
| 30 vs 0 | −1.41 | 0.11 | <.0001 | <.0001 |

[1]contrasts from ANOVA model for repeated measures adjusted with Dunnett test

The data showed a significant decrease in non-adherent dandruff score on D9 (p<0.0001), on D15 (p<0.0001) and on D30 (p<0.0001).

Example 7

Effect of *Epilobium angustifolium* Extract on Adherent Dandruff

Three days after the last shampoo, the technician evaluated, under medical control, the adherent dandruff using a score from 0 to 5 according to Table II. The anti-adherent dandruff effect of the active shampoo prepared as described in Example 2 was evaluated at days D0, D3, D9, D15 and D30.

Figure 3:
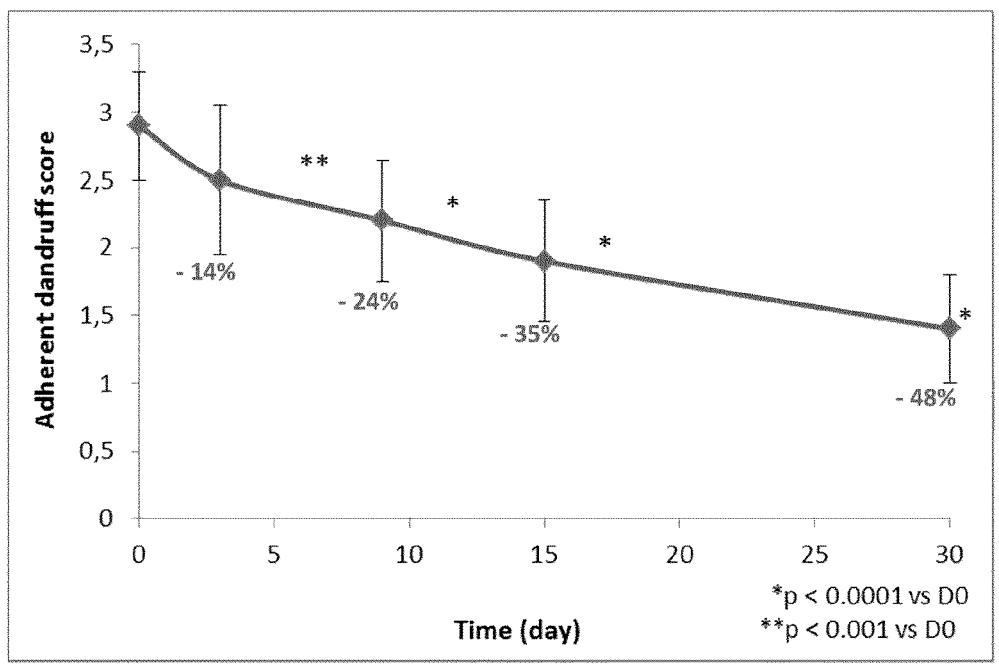
FIG. 3 presents the evolution of the average score (n=24) for adherent dandruff (±2 SEM) over time in human subjects treated with an active shampoo comprising the *E. angustifolium* extract prepared as described in Example 2.
Figure 4:
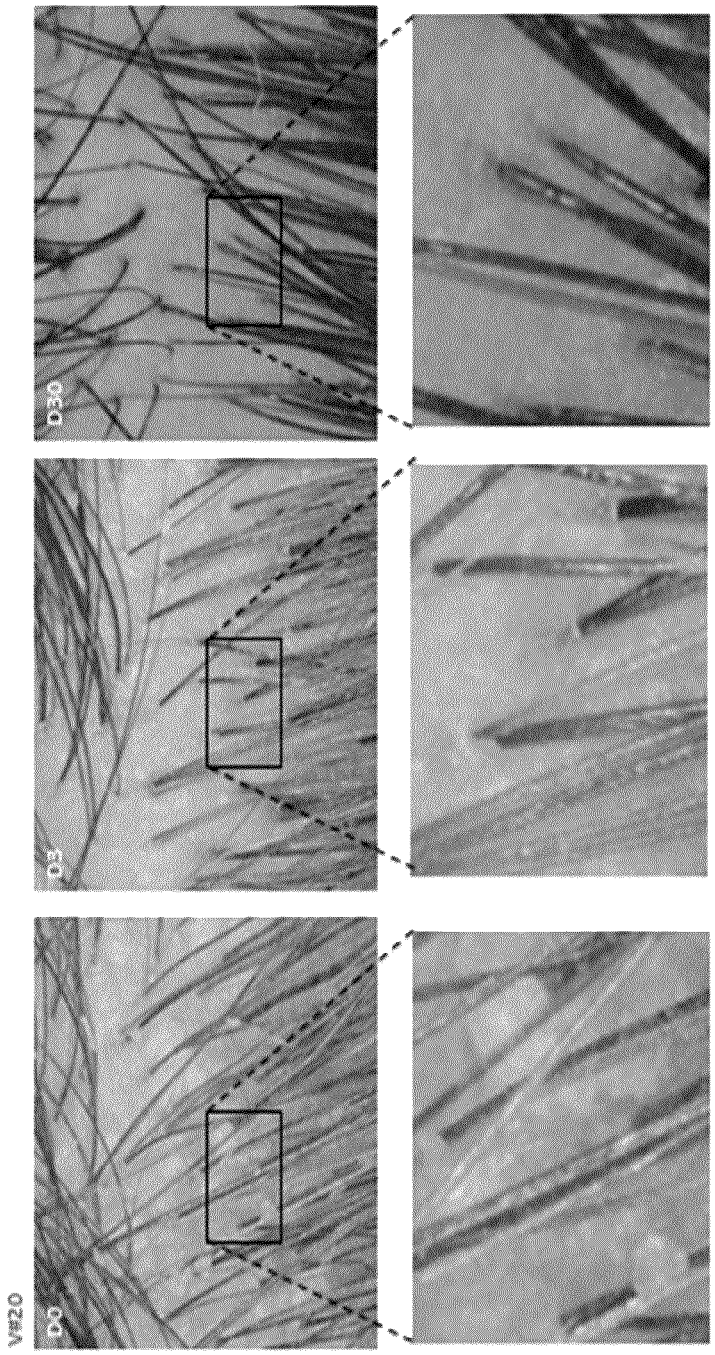
FIG. 4 presents photographs of representative subjects' scalp (subjects #20, #14 and #22, See Table I below) treated with an active shampoo comprising the *E. angustifolium* extract at D0, D3 and D30 prepared as described in Example 2.
Figure 4:
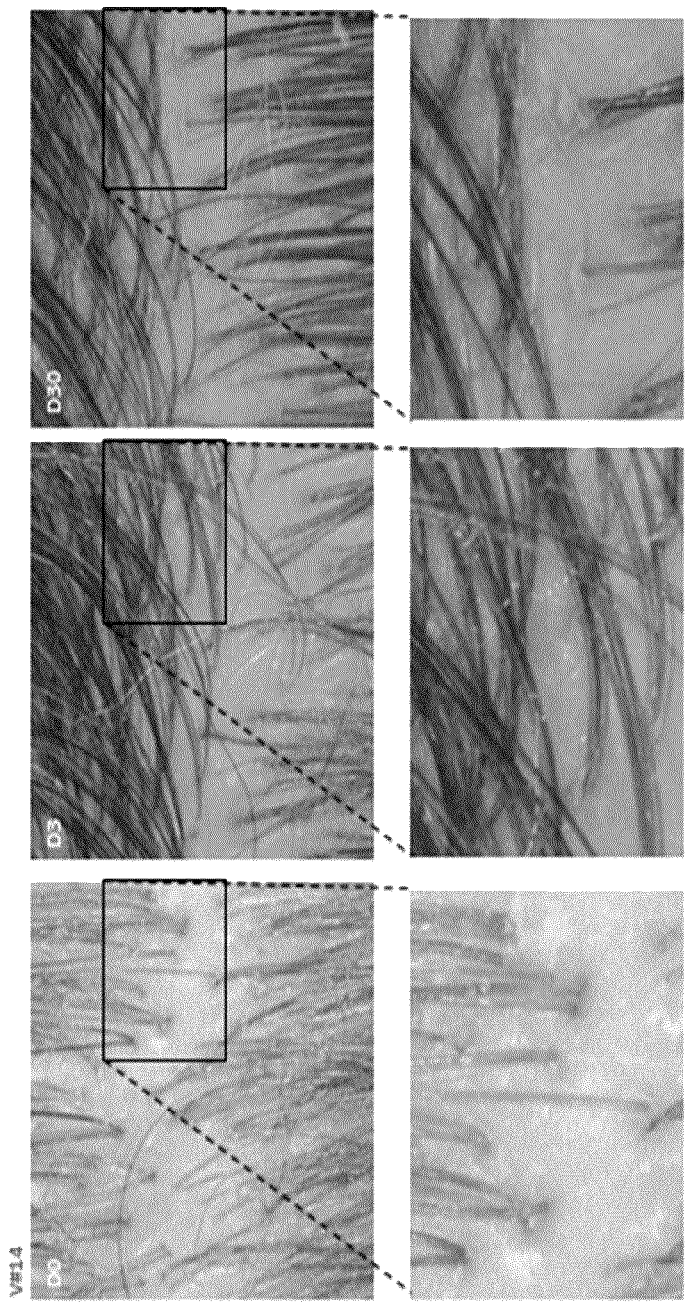
Figure 4:
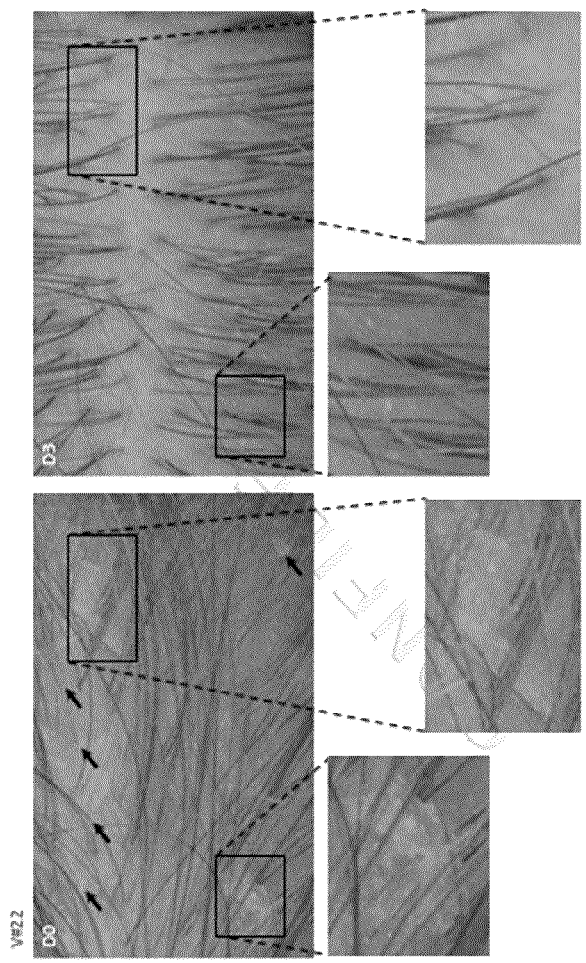

The results are presented in Tables V and VI, as well as in FIGS. 3 and 4.

TABLE V descriptive statistics for adherent dandruff score for each time point (Di).

| Time (Di) | N | N Missing | Mean | Median | Std Dev | Std Error | Minimum | Maximum |
|---|---|---|---|---|---|---|---|---|
| 0 | 24 | 0 | 2.9 | 3.0 | 0.9 | 0.2 | 2.0 | 4.5 |
| 3 | 24 | 0 | 2.5 | 2.5 | 1.1 | 0.2 | 1.0 | 4.5 |
| 9 | 24 | 0 | 2.2 | 2.0 | 0.9 | 0.2 | 0.5 | 4.0 |
| 15 | 24 | 0 | 1.9 | 2.0 | 0.9 | 0.2 | 0.5 | 3.5 |
| 30 | 24 | 0 | 1.4 | 1.0 | 0.8 | 0.2 | 0.0 | 3.0 |

TABLE VI summary of change from baseline for each time point (Di-D0), for adherent dandruff score.

| Comparison (Di vs D0) | Estimate | SEM | Raw p | Adjusted p[(1)] |
|---|---|---|---|---|
| 3 vs 0 | −0.42 | 0.11 | 0.0002 | 0.0008 |
| 9 vs 0 | −0.73 | 0.11 | <.0001 | <.0001 |
| 15 vs 0 | −0.98 | 0.11 | <.0001 | <.0001 |
| 30 vs 0 | −1.51 | 0.11 | <.0001 | <.0001 |

[(1)]contrasts from ANOVA model for repeated measures adjusted with Dunnett test The data showed a significant decrease from baseline (D0) in adherent score on D3 ($p=0.0008$), D9 ($p<0.0001$), D15 ($p<0.0001$) and D30 (with $p<0.0001$).

Representative macrophotographs of 3 subjects' scalps taken on D0, D3 and D30 are shown in FIG. 4. They show a decrease of adherent dandruff over time.

Example 8

Effect of *Epilobium angustifolium* Extract on Sebum Secretion

The quantity of sebum secreted on the skin surface was measured with a COURAGE and KHAZAKA SM 810 Sebumeter™ on D0, D15 and D30 visits.

This photometric method uses a synthetic ribbon applied to the measurement, which becomes transparent when in contact with absorbed lipids. Its transparency increases proportionally with the quantity of sebum.

The total mass of the lipids excreted by the surface unit (in $\mu g/cm^2$) is calculated by reflectometry.

TABLE VII

Statistics for sebum measurement for each time point (Di).

| Time (Di) | N | N Miss | Mean | Median | Std Dev | Std Error | Minimum | Maximum |
|---|---|---|---|---|---|---|---|---|
| 0 | 24 | 0 | 155.2 | 149.0 | 36.8 | 7.5 | 102.0 | 260.0 |
| 15 | 24 | 0 | 65.1 | 69.5 | 22.3 | 4.6 | 17.0 | 102.0 |
| 30 | 23 | 1 | 51.5 | 51.0 | 20.6 | 4.3 | 19.0 | 100.0 |

Figure 5:
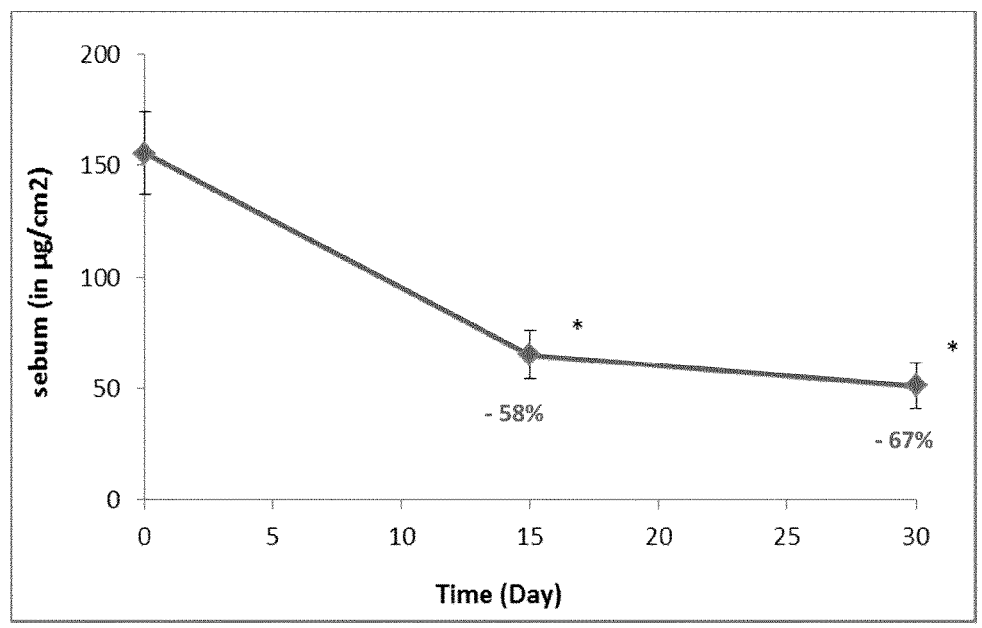
FIG. 5 presents the evolution of average sebum secretion (n=24) (±2 SEM) over time in human subjects treated with an active shampoo comprising the *E. angustifolium* extract prepared as described in Example 2.

The results presented in Table III are also shown in FIG. 5.

TABLE VIII

Summary of change from baseline for each time point (ti-t0), for sebum measurement.

| Comparison | Estimate | SEM | raw p | adjusted p[(1)] |
|---|---|---|---|---|
| D15 vs D0 | 2.85 | 0.27 | <.0001 | <.0001 |
| D30 vs D0 | 4.06 | 0.30 | <.0001 | <.0001 |

[(1)]contrasts from ANOVA model for repeated measures adjusted with Dunnett test The data showed a significant decrease in sebum value from baseline (D0) on D15 ($p<0.0001$) and D30 ($p<0.0001$).

Example 9

Effect of *Epilobium angustifolium* Extract on Pre-Existing Irritation

TABLE IX

Descriptive statistics for irritation score for each time point (Di).

| Time (Di) | N | N Missing | Mean | Median | Std Dev | Std Error | Minimum | Maximum |
|---|---|---|---|---|---|---|---|---|
| 0 | 24 | 0 | 0.1 | 0.0 | 0.5 | 0.1 | 0.0 | 2.0 |
| 3 | 24 | 0 | 0.0 | 0.0 | 0.0 | 0.0 | 0.0 | 0.0 |
| 9 | 24 | 0 | 0.0 | 0.0 | 0.1 | 0.0 | 0.0 | 0.5 |
| 15 | 24 | 0 | 0.0 | 0.0 | 0.0 | 0.0 | 0.0 | 0.0 |
| 30 | 24 | 0 | 0.0 | 0.0 | 0.0 | 0.0 | 0.0 | 0.0 |

As can be seen from the data in Table IX, only 3 subjects (12.5%) had irritation signs (scores between 0.5 and 2) at baseline (D0). From D3 to D30, no irritation signs were observed, except on D9 where one subject had a score of 0.5.

TABLE X

Distribution (in frequency and percentage) of average score for irritation over time.

| Score | | TIME (Di) 0 | 3 | 9 | 15 | 30 |
|---|---|---|---|---|---|---|
| 0 | N | 21 | 24 | 23 | 24 | 24 |
|   | % | 87 | 100 | 95.83 | 100 | 100 |
| 0.5 | N | 1 | 0 | 1 | 0 | 0 |
|   | % | 4.17 | 0 | 4.17 | 0 | 0 |
| 1 | N | 1 | 0 | 0 | 0 | 0 |
|   | % | 4.17 | 0% | 0 | 0 | 0 |

TABLE X-continued

Distribution (in frequency and percentage) of average score for irritation over time.

| Score | | TIME (Di) | | | | |
|---|---|---|---|---|---|---|
| | | 0 | 3 | 9 | 15 | 30 |
| 2 | N | 1 | 0 | 0 | 0 | 0 |
| | % | 4.17 | 0 | 0 | 0 | 0 |
| p-value° (comparison with D0) | | | <0.0001 | 0.1946 | <0.0001 | <0.0001 |

°p-value from GEE model

In comparison with baseline (D0), a significant decrease in irritation was observed on D3 (p<0.0001), D15 (p<0.0001) and D30 (p<0.0001). Because only a few subjects had irritation, a categorial data analysis was performed and is shown in Table X.

Example 10

Effect of *Epilobium angustifolium* Extract on Pre-Existing Erythema

TABLE XI

Descriptive statistics for erythema score for each time point (Di).

| Time (Di) | N | N Missing | Mean | Median | Std Dev | Std Error | Minimum | Maximum |
|---|---|---|---|---|---|---|---|---|
| 0 | 24 | 0 | 0.4 | 0.0 | 0.7 | 0.2 | 0.0 | 2.0 |
| 3 | 24 | 0 | 0.3 | 0.0 | 0.6 | 0.1 | 0.0 | 2.0 |
| 9 | 24 | 0 | 0.2 | 0.0 | 0.4 | 0.1 | 0.0 | 1.5 |
| 15 | 24 | 0 | 0.2 | 0.0 | 0.5 | 0.1 | 0.0 | 1.5 |
| 30 | 24 | 0 | 0.0 | 0.0 | 0.0 | 0.0 | 0.0 | 0.0 |

TABLE XII

Distribution (in frequency and percentage) of average score for erythema (±2 SEM) over time.

| Score | | TIME (Di) | | | | |
|---|---|---|---|---|---|---|
| | | 0 | 3 | 9 | 15 | 30 |
| 0 | N | 18 | 18 | 20 | 20 | 24 |
| | % | 75.00 | 75.00 | 83.33 | 83.33 | 100.00 |
| 0.5 | N | 0 | 1 | 2 | 1 | 0 |
| | % | 0% | 4.17 | 8.33 | 4.17 | 0 |
| 1 | N | 2 | 3 | 0 | 1 | 0 |
| | % | 8.33 | 12.50 | 0 | 4.17 | 0 |
| 1.5 | N | 1 | 1 | 2 | 2 | 0 |
| | % | 4.17 | 4.17 | 8.33 | 8.33 | 0 |
| 2 | N | 3 | 1 | 0 | 0 | 0 |
| | % | 12.50 | 4.17 | 0 | 0 | 0 |
| p-value° (comparison with D0) | | | 0.9903 | 0.3429 | 0.2467 | <0.0001 |

°p-value from GEE model

The erythema score data showed that the proportion of subjects with a sign of erythema was 25% at baseline (D0) and D3 (scores from 0.5 to 2). On D9 and D15, this proportion was lower with 16.7% of subjects having erythema.

Moreover, the data revealed that no signs of erythema was observed on D30, in comparison with baseline (D0) this decrease was significant with p<0.0001. Because only a few subjects had erythema, a categorial data analysis was performed and is shown in Table XII.

Example 11

Effect of the *Epilobium angustifolium* Extract on Induced Erythema (Irritation and Redness)

Additional experiments were conducted to determine the effect of the *Epilobium angustifolium* extract on induced erythema (redness and irritation).

Eight volunteers (women, 18 to 60 years old) with skin types I-III were used. Lactic acid (15%) was applied on their scalp for 4 hours to induce redness and irritation.

A 3% (v/v) dilution of the *E. angustifolium* solution prepared as described in Example 1, or a 1% hydrocortisone lotion was then applied, and erythema was measured after 30 minutes, 1 hour and 24 hours (a* value determination using chromametry).

Figure 6:
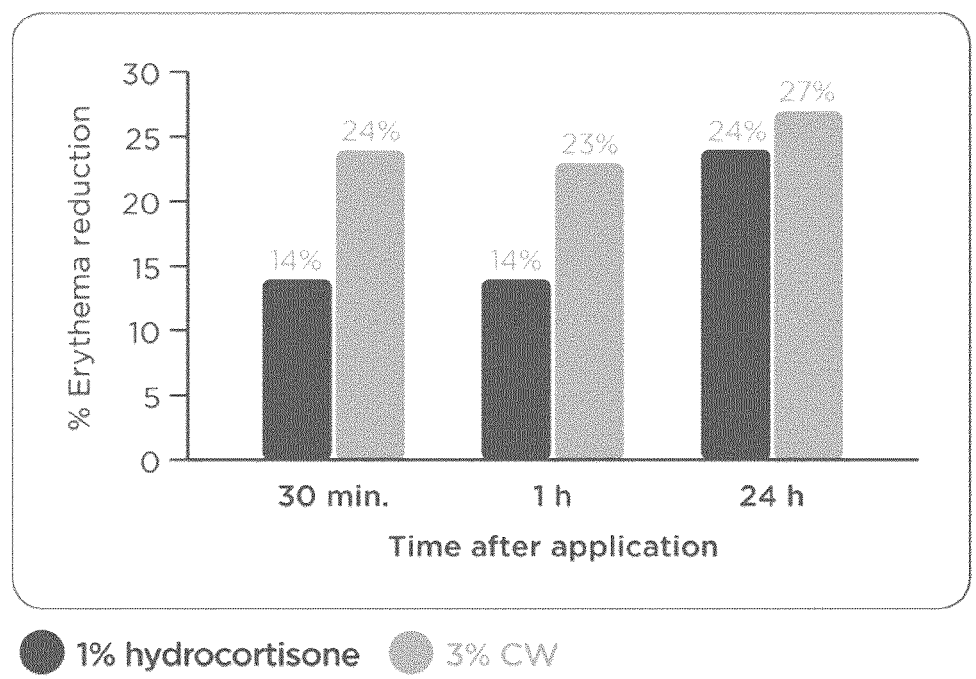
FIG. 6 presents the effect of a 3% v/v dilution of the *E. angustifolium* solution prepared as described in Example 1 on pre-irritated human skin.

The results in FIG. 6 show that a 3% (v/v) dilution of the solution prepared as described in Example 1 reduces erythema by 24% after 30 minutes, by 23% after 1 hour, and by 27% after 24 hours.

Example 12

Cutaneous Tolerance of *Epilobium angustifolium* Extract

The cutaneous tolerance of the active shampoo prepared as described in Example 2 was evaluated by a clinical examination by a dermatologist before and after three times a week application on hair and scalp during 30 days. Cutaneous tolerance was determined at days D0, D3, D9, D15 and D30.

After 3 days of use (D3), two subjects reported itching on the parietal and temporal areas just after application and four subjects reported dandruff or erythema, but these signs were judged not relevant by the dermatologist.

After 9 days of use (D9), three subjects reported dandruff, but these signs were judged not relevant by the dermatologist. After 15 days of use, one subject reported dandruff and erythema, but these signs were judged not relevant by the dermatologist. After 30 days of use, no subject reported any physical, functional or clinical sign. The active shampoo was very well tolerated.

Example 13

Subjective Evaluation Questionnaire

A subjective evaluation was performed by each subject (n=24) to assess the effect of the active shampoo prepared as described in Example 2 before and after application three times a week on hair and scalp for 30 days. Subjects were questioned at days D0 and D30. After D30, subjects responded to a questionnaire to report e.g.: (A) the state of their scalp prior to treatment with the active shampoo ("Before Treatment") with regards to itching, dandruff, and oil hair; (B) when improvement and modification of hair aspect was first observed during the 30-day treatment period with the active shampoo (i.e., beginning, middle, and/or end of treatment) with regards improvement of scalp state, modification of hair's aspect compared to usual, whether they notice an effect on itching, on dandruff, and on re-greasing of hair, whether the active shampoo had a soothing effect, whether the active shampoo had an effect at the level of re-greasing of hair, and their overall satisfaction with the effects of the active shampoo; and (C) whether they would voluntarily continue to use the active shampoo ("Future Use") after the clinical trial. The results from the questionnaire are shown in Table XIII.

TABLE XIII

Synthesis of subjective evaluation (n = 24, 1 subject represents 4.2%)

| (A) BEFORE TREATMENT | |
|---|---|
| Itching: | 12% |
| "a lot" | 4% |
| "enough" | 8% |
| Dandruff: | 25% |
| "a lot" | 8% |
| "enough" | 17% |
| Oily hair: | 25% |
| "a lot" | 8% |
| "enough" | 17% |
| (B) AFTER 30 DAYS OF USE EFFICACY | |
| Improvement of scalp state: | 91% |
| Yes, at the beginning of the treatment | 33% |
| Yes, at the middle of the treatment | 54% |
| Yes, at the end of the treatment | 4% |
| Modification of hair's aspect compared to usually: | 100% |
| Yes, at the beginning of the treatment | 21% |
| Yes, at the middle of the treatment | 46% |
| Yes, at the end of the treatment | 33% |
| Itching | 63% |
| Much less | 25% |
| Less | 38% |
| Dandruff | 83% |
| Much less | 29% |
| Less | 54% |
| Re-greasing of hair | 66% |
| Much less | 33% |
| Less | 33% |
| A positive soothing effect | 46% |
| An effect at the level of re-greasing of hair | 75% |
| Satisfied with the effect of this product | 75% |
| Very satisfied | 25% |
| Satisfied | 50% |
| (C) FUTURE USE OF THE PRODUCT | |
| Would like to continue to use the product | 75% |

In general, the results from the subjective evaluation questionnaire showed that the subjects appreciated the active shampoo for its efficacy (improves scalp state, reduces dandruff and regreasing of hair).

The scope of the claims should not be limited by the preferred embodiments set forth in the examples, but should be given the broadest interpretation consistent with the description as a whole.

REFERENCES

1. ICH TOPIC E6/Note for guidance on Good Clinical Practice—CPMP/ICH/135/95, January 1997.
2. WORLD MEDICAL ASSOCIATION DECLARATION OF HELSINKI/Ethical Principles for Medical Research Involving Human Subjects—Helsinki Declaration (1964) and its successive updates.
3. BROECKS W., BLONDEEL A., DOOMS-GOOSSENS A., ACHTEN G./Cosmetic intolerance—Contact Dermatitis, 1987, 16, 189.
4. ROBERT P., COLL./Dermopharmacologie clinique—EDISEM MALOINE, 1985.
5. Smith K R, Thiboutot D M. Thematic review series: skin lipids. Sebaceous gland lipids: friend or foe? J Lipid Res. 2008 February; 49(2):271-81. Epub 2007 Nov. 1.
6. Ro B I, Dawson T L. The role of sebaceous gland activity and scalp microfloral metabolism in the etiology of seborrheic dermatitis and dandruff. J Investig Dermatol Symp Proc. 2005 December; 10(3):194-7.
7. LENTNER A., WIENERT V. A new method for assessing the gloss of human skin. Skin Pharmacology.—1996; 9, 3: 184-189.
8. SOKAL R. R., ROHLF F. J./Biometry: the principles and practice of statistics in biological research—3rd edn. W.H. Freeman and company, New York, 1995.

The invention claimed is:

1. A method for reducing dandruff, said method comprising applying a composition comprising a therapeutically effective amount of an *Epilobium angustifolium* extract, and a preservative agent on the scalp of a subject in need thereof, wherein the dandruff is reduced on the scalp of the subject as compared to prior to said administration.

2. The method of claim 1, wherein said dandruff is: adherent dandruff; non-adherent dandruff; or a combination thereof.

3. The method of claim 1, wherein said composition is further for reducing or preventing at least one of: hair regreasing; scalp irritation; scalp erythema; and scalp itching.

4. The method of claim 1, wherein said composition is applied at least three times on the scalp of said subject.

5. The method of claim 1, wherein said composition is applied
   (a) every 3 days over at least 9 days;
   (b) every 3 days over at least 12 days;
   (c) every 3 days over at least 15 days;
   (d) every 3 days over at least 18 days;
   (e) every 3 days over at least 21 days;
   (f) every 3 days over at least 24 days;
   (g) every 3 days over at least 27 days; or
   (h) every 3 days over at least 30 days.

6. The method of claim 1, wherein said *Epilobium angustifolium* extract is an aqueous extract.

7. The method of claim 1, wherein the therapeutically effective amount of *Epilobium angustifolium* extract is sufficient to inhibit growth of a *Malassezia* fungus.

8. The method of claim 7, wherein said *Malassezia* fungus is: *Malassezia furfur, Malassezia globosa, Malassezia restricta*, or any combination thereof.

9. The method of claim 1, wherein said therapeutically effective amount of *Epilobium angustifolium* extract is at least 0.069% (w/v) of dry weight *Epilobium angustifolium* extract.

10. The method of claim 1, wherein said therapeutically effective amount of *Epilobium angustifolium* extract is at least 0.25% (w/v) of dry weight *Epilobium angustifolium* extract.

11. The method of claim 1, wherein said composition further comprises a physiologically acceptable carrier.

12. The method of claim 1, wherein said composition further comprises an emulsified oil.

13. The method of claim 1, wherein said preservative is sodium metabisulfite and/or phenoxyethanol.

14. The method of claim 1, wherein said composition is formulated as a shampoo, a spray, a cream, a lotion, a mask, or a gel.

15. The method of claim 1, further comprising applying on the scalp of said subject in need thereof at least one other agent useful to treat or prevent a scalp condition or disorder or at least one symptom thereof.

16. The method of claim 15, wherein said at least one other agent useful to treat or prevent a scalp condition or disorder or at least one symptom thereof is: an anti-dandruff agent, an anti-sebum agent, an anti-irritation agent or an antioxidant.

17. The method of claim 15, wherein said at least one other agent useful to treat or prevent a scalp condition or disorder or at least one symptom thereof is in said composition.

\* \* \* \* \*